(12) United States Patent
Tao et al.

(10) Patent No.: US 10,408,775 B2
(45) Date of Patent: Sep. 10, 2019

(54) SENSOR ARRANGEMENTS AND METHODS OF OPERATING A SENSOR ARRANGEMENT

(71) Applicant: AGENCY FOR SCIENCE, TECHNOLOGY AND RESEARCH, Singapore (SG)

(72) Inventors: Jifang Tao, Singapore (SG); Alex Yuan-dong Gu, Singapore (SG); Hong Cai, Singapore (SG); Junfeng Song, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 15/576,840

(22) PCT Filed: May 25, 2016

(86) PCT No.: PCT/SG2016/050247
§ 371 (c)(1),
(2) Date: Nov. 26, 2017

(87) PCT Pub. No.: WO2016/190816
PCT Pub. Date: Dec. 1, 2016

(65) Prior Publication Data
US 2018/0164236 A1     Jun. 14, 2018

(30) Foreign Application Priority Data

May 26, 2015     (SG) .............................. 10201504118R

(51) Int. Cl.
*G01N 25/68* (2006.01)
*G01N 21/41* (2006.01)
(Continued)

(52) U.S. Cl.
CPC .............. *G01N 25/68* (2013.01); *G01N 21/27* (2013.01); *G01N 21/41* (2013.01); *G01N 21/63* (2013.01);
(Continued)

(58) Field of Classification Search
CPC ........ G01B 25/68; G01N 21/27; G01N 21/41; G01N 21/63; G01N 2021/435; G01N 2021/7776; G01N 2021/7779
See application file for complete search history.

(56) References Cited

U.S. PATENT DOCUMENTS 3,611,788 A    10/1971   Amelkin et al.
4,335,597 A    6/1982    Hayes, Jr. et al.
(Continued)

FOREIGN PATENT DOCUMENTS

CN         102520019 A      6/2012

OTHER PUBLICATIONS

Korvink et al., "Accurate 3D capacitance evaluation in integrated capacitive humidity sensors," Sens. Mater., 4(6): 323-335, 1993.
(Continued)

*Primary Examiner* — Dominic J Bologna
(74) *Attorney, Agent, or Firm* — Womble Bond Dickinson (US) LLP

(57) ABSTRACT

According to various embodiments, there is provided a sensor arrangement including a filter configured to provide an output signal having an output wavelength, the output wavelength having a dependence on a temperature of the filter; a temperature module configured to change the temperature of the filter; a controller circuit configured to control the temperature module for changing the temperature of the filter until the output wavelength increases with decreasing temperature; and a determination circuit configured to determine a dew point of an environment surround-
(Continued)

ing the sensor arrangement, based on a minimum value of the output wavelength and the dependence.

20 Claims, 10 Drawing Sheets

(51) Int. Cl.
  *G01N 21/27* (2006.01)
  *G01N 21/63* (2006.01)
  *G01N 21/43* (2006.01)
  *G01N 21/77* (2006.01)

(52) U.S. Cl.
  CPC ............. *G01N 2021/435* (2013.01); *G01N 2021/7776* (2013.01); *G01N 2021/7779* (2013.01)

(56) References Cited

U.S. PATENT DOCUMENTS

| | | | |
|---|---|---|---|
| 6,126,311 A | 10/2000 | Schuh | |
| 6,223,588 B1 | 5/2001 | Burgass et al. | |
| 6,926,439 B2 | 8/2005 | Zlochin | |
| 2010/0086261 A1* | 4/2010 | Tanaka | G02B 6/12007 385/88 |
| 2010/0322280 A1 | 12/2010 | Kwon et al. | |
| 2012/0200855 A1* | 8/2012 | Bonyuet | G01J 3/02 356/418 |
| 2013/0139587 A1 | 6/2013 | Le Neel et al. | |
| 2013/0161496 A1* | 6/2013 | Akiyama | G02F 1/0147 250/227.23 |
| 2014/0253917 A1* | 9/2014 | Heidrich | G01N 21/39 356/300 |

OTHER PUBLICATIONS

Jachowicz et al., "A thin film capacitance humidity sensor," Sens. Actuators, 2: 171-186, 1981.
Seiyama et al., "Ceramic humidity sensors," Sens. Actuators, 4: 85-96, 1983.
Kimura, "A new method to measure the absolute—humidity independently of the ambient temperature," Sens. Actuators B, 33: 156-160, 1996.
Jain et al., "Magnetoacoustic remote query temperature and humidity sensors," Smart Mater. Struct., 9: 502-510, 2000.
Tan et al., Y. Chae, and M. A. P. Pertijs, "A 1.2V 8.3nJ CMOS humidity sensor for RFID applications," IEEE J. Solid-State Circuits, 48(10): 2469-2477, 2013.
Konvalina et al., "Sensors for breath testing: from nanomaterials to comprehensive disease detection," Accounts Chemical Research, 47(1): pp. 66-76, 2014.
Sorli et al., "Fast humidity sensor for high range 80-95% RH," Sen. Actuators A, 100: 24-31, 2002.
Graichen et al., "Automatic dew-point temperature sensor," J. Appl. Physiology, 52(6): 1658-1660, 1982.
Hixson et al., "Accurate determination of dew point," Industrial and Engineering Chemistry, 10(5): 235-240, 1938.
Jonker et al., "The humidity calibration facility of the national metrology institute of south africa," Int. J. Thermophysics, 29(5): 1644-1651, 2008.
Blumenthal, "High response dew point measurement system for a supersonic wind tunnel," NASA Contractor Report 198453, 1996.
Avila et al., "Dew-point curves of natural gas. measurement and modeling," Ind. Eng. Chem. Res., 45: 5179-5184, 2006.
Usachov et al., "Membrane contactor air conditioning system: experience and prospects," Separation and Purification Technology, 57(3): 502-506, 2007.
Fan et al., "Effects of aerosols and relative humidity on cumulus clouds," J. Geophysical Research, 112: D14204, 15 pages, 2007.
Han et al., "Carbon nanotube based humidity sensor on cellulose paper," J. Phys. Chem. C, 116: 22094-22097, 2012.
Bi et al., "Ultrahigh humidity sensitivity of graphene oxide," Scientific Reports, 3: 02714, Sep. 19, 2013.
Kim et al., "Silicon photonics temperature sensor employing a ring resonator manufactured using a standard CMOS process," Opt. Express, 18:(21): 22215-22221, 2010.
Densmore et al., "Compact and low power thermo-optic switch using folded silicon waveguides," Opt. Express, 17(13): 10457-10465, 2009.
Tinker et al., "Thermo-optic photonic crystal light modulator," Appl. Phys. Lett., 86: 221111, 3 pages, 2005.
Cunningham et al., "Highly-efficient thermally-tuned resonant optical filters," Opt. Express, 18(18): 19055-19063, 2010.
Fan et al., "Sensitive optical biosensors for unlabeled target: A review," Analytica Chimica Acta, 620(1-2): 8-26, 2008.
Ksendzov et al., "Integrated optics ring-resonator sensors for protein detection," Opt. Letters, 30(24): 3344-3346, 2005.
Li et al., "High sensitive and stable humidity nanosensors based on LiCl doped TiO2 electrospun nanofibers," 5 pages, 2008.
Nagasaki et. al, "Dew Condensation Sensor Based on Surface Plasmon Resonance of Periodic Silver Nanostructure on AT-cut Quartz Crystal," Proceedings of SPIE, 7544, 75442O, 7 pages, 2010.
IP Office of Singapore, Notification of Transmittal of the International Search Report and the Written Opinion of the International Searching Authority, or the Declaration, with the International Search Report and Written Opinion dated Jul. 21, 2016 for related International Application No. PCT/SG2016/050247 (11 pgs).
IP Office of Singapore, International Preliminary Report on Patentability including the Chapter II Demand under Article 34, dated Feb. 3, 2017 for related International Application No. PCT/SG2016/050247 (16 pgs).
Tao J. et al., "A novel photonic dew-point hygrometer with ultrahigh accuracy." 2016 IEEE 29th International Conference on Micro Electro Mechanical Systems (MEMS), Jan. 28, 2016, pp. 893-896 <DOI: 10.1109/MEMSYS.2016.7421774>.
Nie J. et al., "Dew point and relative humidity measurement using a quartz resonant sensor." Journal of Microsystem Technologies, Sep. 22, 2013, vol. 20, No. 7, pp. 1311-1315 <DOI: 10.1007/S00542-013-1914-9>.
Su-Yong Kwon, et al., "Accurate dew-point measurement over a wide temperature range using a quartz crystal microbalance dew-point sensor," Measurement Science and Technology, vol. 19, No. 11, 7 pgs. (Oct. 6, 2008).
Tao J. F. et al., "Demonstration of a Photonic-Based Linear Temperature Sensor." *IEEE Phontonics Technology Letters*, Apr. 1, 2015, vol. 27, No. 7, pp. 767-769 <DOI: 10.1109/LPT.2015.2392107>.
Jing Nie, et al., "Dew point measurement using a quartz crystal sensor," Instrumentation and Measurement Technology Conference (I2mTC), 2013 IEEE International, 4 pgs. (May 6-9, 2013).

\* cited by examiner

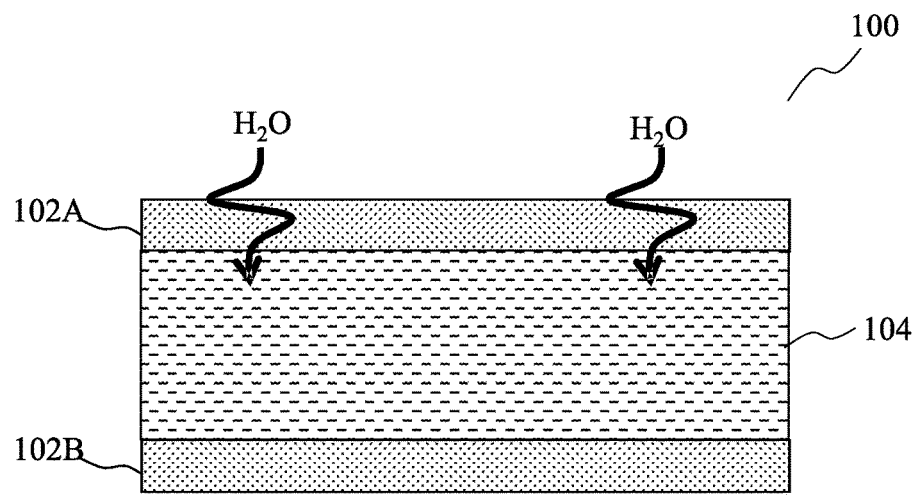
FIG. 1 – Prior Art
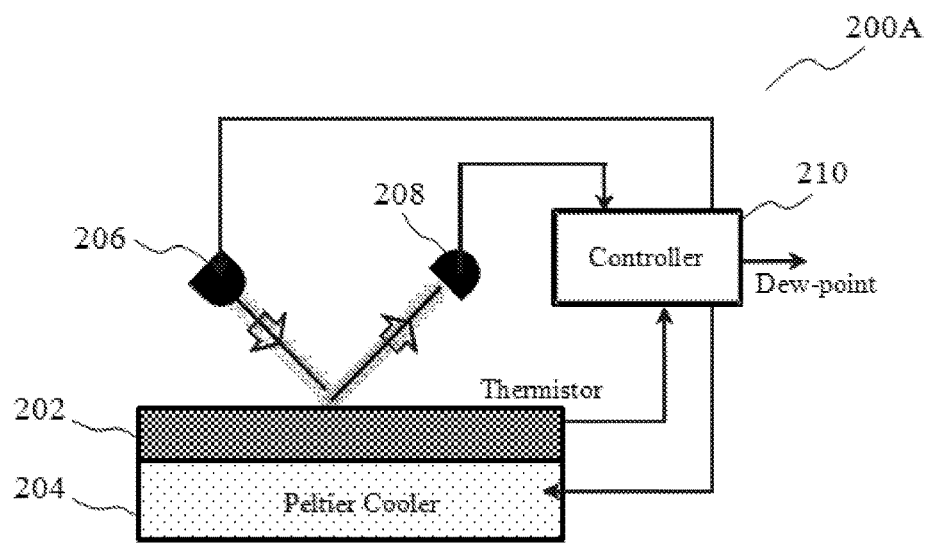
FIG. 2A – Prior Art

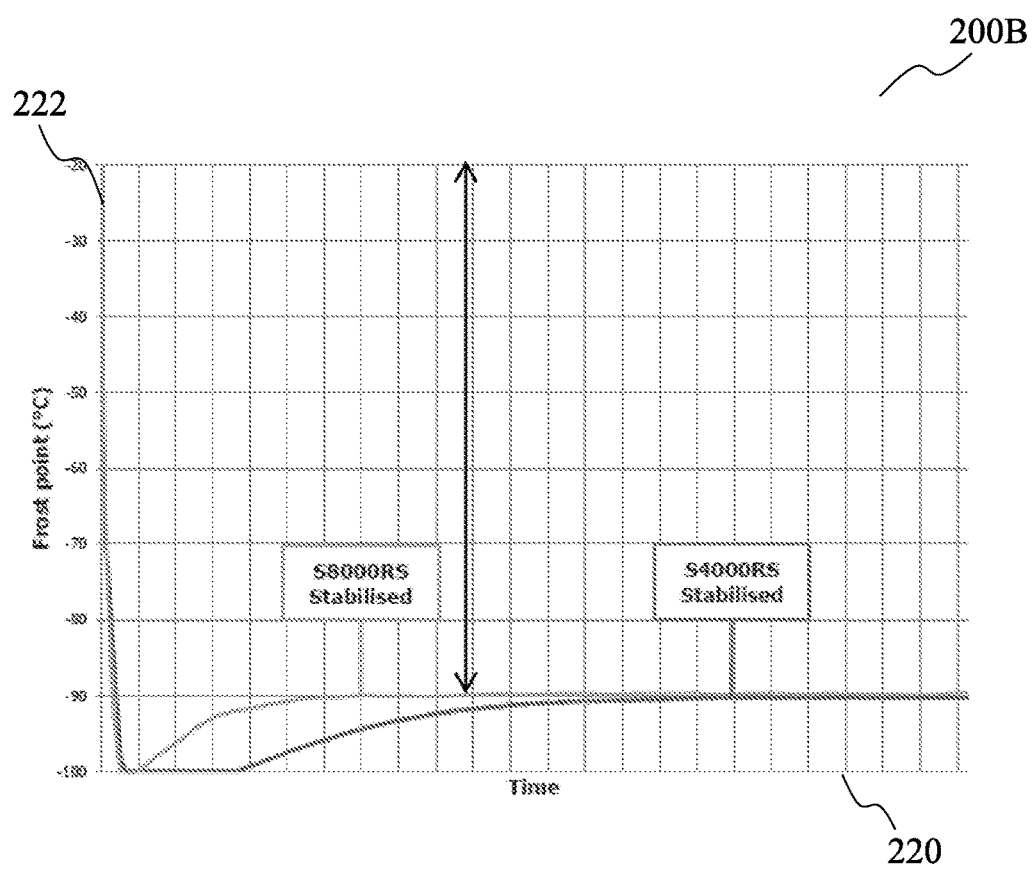
FIG. 2B – Prior Art

| Standard deviation | |
|---|---|
| Resonance wavelength (nm) | 0.0125 |
| Dew-point temperature (° C) | 0.19 |
| Relative Humidity (%) | +/- 0.13 |

SENSOR ARRANGEMENTS AND METHODS OF OPERATING A SENSOR ARRANGEMENT

CROSS-REFERENCE TO RELATED APPLICATIONS

This patent application is a U.S. National Phase Application under 35 U.S.C. § 371 of International Application No. PCT/SG2016/050247, filed on 25 May 2016, entitled, SENSOR ARRANGEMENTS AND METHODS OF OPERATING A SENSOR ARRANGEMENT, which claims the benefit of Singapore Patent Application number 10201504118R filed 26 May 2015, the entire contents of which were incorporated herein by reference for all purposes

TECHNICAL FIELD

The present invention relates to sensor arrangements and methods of operating a sensor arrangement.

BACKGROUND

Various types of humidity sensors have been developed over the years. A cost-effective miniaturized solution is to employ a solid state sensing film that interacts with water vapor to convert the water vapor concentration into an electrical signal. Techniques for converting the water vapor concentration into electrical signals include capacitive sensing, thermoelectric sensing and magnetoelastic sensing. A typical electrical humidity sensor may sense water vapor concentration, by having a capacitance or impedance between two electrodes. The capacitance of impedance may vary with the relative permittivity of a polymer film. The relative permittivity of the polymer film may be sensitive to an amount of water vapor absorbed by the polymer film. The typical accuracy of this type of sensors may range from ±1.7% to ±5%, which can meet the requirements in some consumer electronics, for example for use in environmental sensing and medical devices for breath testing. Another method for measuring relative humidity may be to use a "chilled-mirror" dew-point hygrometer. A "chilled-mirror" dew-point hygrometer may include a miniature polished mirror that may be cooled by a Peltier thermoelectric heat pump until the mirror reaches the dew-point of the water vapor under test. When the dew point temperature has been reached, condensation will begin to form on the mirror surface. The "chilled-mirror" dew-point hygrometer may include an electro-optical loop to detect a reduction of the light intensity reflected from the mirror surface and thereby, detect that condensation. The typical accuracy of such a dew-point hygrometer may be ±0.1° C. according to relative humidity accuracy of ±0.014% at a relative humidity of 1%. The high accuracy of a "chilled-mirror" dew-point hygrometer may allow it to be applied to a range of high-end applications including metrology laboratories, aerospace, natural gas, petrochemical and meteorology. However, there are many barriers to using the "chilled-mirror" dew-point hygrometer, including its high cost, large size and slow response rate. Other potential disruptive solutions for high accuracy detection of relative humidity include carbon nanotubes and graphene which exhibit very high humidity sensitivity. However, such solutions still require further development in order to be understood and applied to practical applications.

As such, there is a need for a humidity sensor that can achieve high accuracy with a relatively fast response rate, while being relatively small size and being available at a low cost.

SUMMARY

According to various embodiments, there may be provided a sensor arrangement including a filter configured to provide an output signal having an output wavelength, the output wavelength having a dependence on a temperature of the filter; a temperature module configured to change the temperature of the filter; a controller circuit configured to control the temperature module for changing the temperature of the filter until the output wavelength increases with decreasing temperature; and a determination circuit configured to determine a dew point of an environment surrounding the sensor arrangement, based on a minimum value of the output wavelength and the dependence.

According to various embodiments, there may be provided a sensor arrangement including a filter configured to provide an output signal having an output wavelength, the output wavelength having a dependence on a temperature of the filter, wherein the dependence comprises a proportionality constant having a first value; a temperature module configured to change the temperature of the filter; a controller circuit configured to control the temperature module for changing the temperature of the filter until the proportionality constant changes from the first value to a second value; and a determination circuit configured to determine a dew point of an environment surrounding the sensor arrangement, based on the temperature of the filter when the proportionality constant changes from the first value to the second value.

According to various embodiments, there may be provided a method of operating a sensor arrangement, the method including providing an output signal having an output wavelength using a filter, wherein the output wavelength has a dependence on a temperature of the filter; changing the temperature of the filter using a temperature module; controlling the temperature module to change the temperature of the filter until the output wavelength increases with decreasing temperature, using a controller circuit; and determining a dew point of an environment surrounding the sensor arrangement, based on a minimum value of the output wavelength and the dependence.

According to various embodiments, there may be provided a method of operating a sensor arrangement, the method including providing an output signal having an output wavelength using a filter, wherein the output wavelength has a dependence on a temperature of the filter, wherein the dependence comprises a proportionality constant having a first value; changing the temperature of the filter using a temperature module; controlling the temperature module to change the temperature of the filter until the proportionality constant changes from the first value to a second value, using a controller circuit; and determining a dew point of an environment surrounding the sensor arrangement, based on the temperature of the filter when the proportionality constant changes from the first value to the second value.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments are described with reference to the following drawings, in which:

FIG. 1 shows an electrical humidity sensor belonging to the state of the art.

FIG. 2A shows a "chilled-mirror" dew-point hygrometer belonging to the state of the art.

FIG. 2B shows a graph showing a relationship between frost point and time.

DESCRIPTION

Figure 3A:
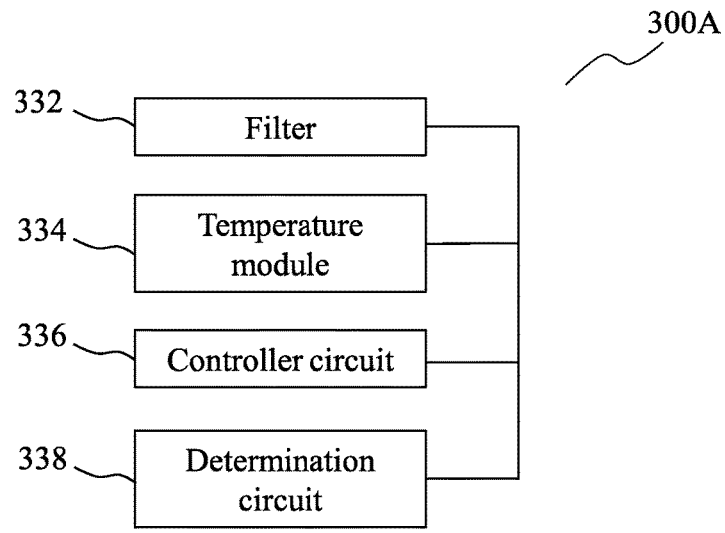
FIG. 3A shows a sensor arrangement according to various embodiments.

Embodiments described below in context of the devices are analogously valid for the respective methods, and vice versa. Furthermore, it will be understood that the embodiments described below may be combined, for example, a part of one embodiment may be combined with a part of another embodiment.

In this context, the sensor arrangement as described in this description may include a memory which is for example used in the processing carried out in the sensor arrangement. A memory used in the embodiments may be a volatile memory, for example a DRAM (Dynamic Random Access Memory) or a non-volatile memory, for example a PROM (Programmable Read Only Memory), an EPROM (Erasable PROM), EEPROM (Electrically Erasable PROM), or a flash memory, e.g., a floating gate memory, a charge trapping memory, an MRAM (Magnetoresistive Random Access Memory) or a PCRAM (Phase Change Random Access Memory).

In an embodiment, a "circuit" may be understood as any kind of a logic implementing entity, which may be special purpose circuitry or a processor executing software stored in a memory, firmware, or any combination thereof. Thus, in an embodiment, a "circuit" may be a hard-wired logic circuit or a programmable logic circuit such as a programmable processor, e.g. a microprocessor (e.g. a Complex Instruction Set Computer (CISC) processor or a Reduced Instruction Set Computer (RISC) processor). A "circuit" may also be a processor executing software, e.g. any kind of computer program, e.g. a computer program using a virtual machine code such as e.g. Java. Any other kind of implementation of the respective functions which will be described in more detail below may also be understood as a "circuit" in accordance with an alternative embodiment.

In the specification the term "comprising" shall be understood to have a broad meaning similar to the term "including" and will be understood to imply the inclusion of a stated integer or step or group of integers or steps but not the exclusion of any other integer or step or group of integers or steps. This definition also applies to variations on the term "comprising" such as "comprise" and "comprises".

In order that the invention may be readily understood and put into practical effect, particular embodiments will now be described by way of examples and not limitations, and with reference to the figures.

Various embodiments are provided for devices, and various embodiments are provided for methods. It will be understood that basic properties of the devices also hold for the methods and vice versa. Therefore, for sake of brevity, duplicate description of such properties may be omitted.

It will be understood that any property described herein for a specific device may also hold for any device described herein. It will be understood that any property described herein for a specific method may also hold for any method described herein. Furthermore, it will be understood that for any device or method described herein, not necessarily all the components or steps described must be enclosed in the device or method, but only some (but not all) components or steps may be enclosed.

In the context of various embodiments, the phrase "relative humidity" may be but is not limited to being interchangeably referred to by its abbreviation "RH".

In the context of various embodiments, "dew-point temperature" may be but is not limited to being interchangeably referred to "dew point temperature", "dew point", $T_{DP}$ or TDP.

Various types of humidity sensors have been developed over the years. A cost-effective miniaturized solution is to employ a solid state sensing film that interacts with water vapor to convert the water vapor concentration into an electrical signal. Techniques for converting the water vapor concentration into electrical signals include capacitive sensing, thermoelectric sensing and magnetoelastic sensing. A typical electrical humidity sensor may sense water vapor concentration, by having a capacitance or impedance between two electrodes. The capacitance of impedance may vary with the relative permittivity of a polymer film. The relative permittivity of the polymer film may be sensitive to an amount of water vapor absorbed by the polymer film. The typical accuracy of this type of sensors may range from ±1.7% to ±5%, which can meet the requirements in some consumer electronics, for example for use in environmental sensing and medical devices for breath testing. Another method for measuring relative humidity may be to use a "chilled-mirror" dew-point hygrometer. A "chilled-mirror" dew-point hygrometer may include a miniature polished mirror that may be cooled by a Peltier thermoelectric heat pump until the mirror reaches the dew-point of the water vapor under test. When the dew point temperature has been reached, condensation will begin to form on the mirror surface. The "chilled-mirror" dew-point hygrometer may include an electro-optical loop to detect a reduction of the light intensity reflected from the mirror surface and thereby, detect that condensation. The typical accuracy of such a dew-point hygrometer may be ±0.1° C. according to relative humidity accuracy of ±0.014% at a relative humidity of 1%. The high accuracy of a "chilled-mirror" dew-point hygrometer may allow it to be applied to a range of high-end applications including metrology laboratories, aerospace, natural gas, petrochemical and meteorology. However, there are many barriers to using the "chilled-mirror" dew-point hygrometer, including its high cost, large size and slow response rate. Other potential disruptive solutions for high accuracy detection of relative humidity include carbon nanotubes and graphene which exhibit very high humidity sensitivity. However, such solutions still require further development in order to be understood and applied to practical applications. As such, there is a need for a humidity sensor that can achieve high accuracy with a relatively fast response rate, while being relatively small size and being available at a low cost.

FIG. 1 shows an electrical humidity sensor 100 belonging to the state of the art. The electrical humidity sensor 100 may be a miniaturized electrical sensor for measuring relative humidity in the air. The electrical humidity sensor 100 may function based on the principle of sensing variations in capacitance or impedance. The electrical humidity sensor 100 may include a top electrode 102A and a bottom electrode 102B. The top electrode 102A and the bottom electrode 102B may sandwich a polymer film 104. The top electrode 102A and the bottom electrode 102B may be porous so as to allow water vapor in the surrounding environment to be absorbed into the polymer film 104. The permittivity of the polymer film 104 may change as the amount of absorbed water vapor changes. The change in permittivity of the polymer film 104 may cause the capacitance or impedance between the top electrode 102A and the bottom electrode 102B to change. The accuracy of the humidity sensor 100 is typically low and may be in the range of about ±1.7% to ±5%. This accuracy level may not be sufficient for high-end applications such as metrology laboratories, aerospace, natural gas, petrochemical and meteorology.

FIG. 2A shows a "chilled-mirror" dew-point hygrometer 200A belonging to the state of the art. The "chilled-mirror" dew-point hygrometer 200A may include a mirror 202, a cooler 204, a light source 206, a light detector 208 and a controller 210. The mirror 202 may be a miniature polished mirror. The cooler 204 may be a Peltier thermoelectric heat pump. The mirror 202 may be cooled by the cooler 204 until the mirror 202 reaches the dew-point of the water vapor under test. When the temperature has been reached, condensation will begin to form on the surface of the mirror 202. A light source 206 may be used to direct a beam of light onto the surface of the mirror 202, while a light detector 208 may be positioned to receive the light that is reflected off the surface of the mirror 202. As condensation is formed on the surface of the mirror 202, the intensity of the reflected light is reduced. The light detector 208 and the controller 210 may be part of an electro-optical loop for detecting that condensation is formed by detecting a reduction of the light intensity reflected from the mirror surface. The typical accuracy of the "chilled-mirror" dew-point hygrometer 200A may be about ±0.1° C. according to relative humidity accuracy of ±0.014% at relative humidity 1%. While the "chilled-mirror" dew-point hygrometer 200A may achieve high accuracy, its high cost, large size and slow response may create barriers for its adoptions in practical applications. Due to the need for a bulky chilled mirror and cooling system, the "chilled-mirror" dew-point hygrometer 200A may be large in size. Also, the large thermal capacitance of bulky chilled mirror and cooling system may also cause the "chilled-mirror" dew-point hygrometer 200A to have a long response time. The "chilled-mirror" dew-point hygrometer 200A may also be costly, often costing more than US$30,000 for a system that is able to achieve a relative humidity (RH) accuracy of about ±0.3% accuracy.

FIG. 2B shows a graph 200B showing a relationship between frost point and time, used in a temperature sensor based dew point humidity sensor, such as the "chilled-mirror" hygrometer 200A, for determining RH. The graph 200B includes a horizontal axis 220 indicating time; and a vertical axis 222 indicating frost point in degrees Celsius (° C.). In the traditional temperature sensor based dew point humidity sensor, the RH is determined based on the frost point.

FIG. 3A shows a sensor arrangement 300A according to various embodiments. The sensor arrangement 300A may include a filter 332 configured to provide an output signal having an output wavelength, the output wavelength having a dependence on a temperature of the filter 332. The dependence may include a proportionality constant having a first value. The sensor arrangement 300A may further include a temperature module 334 configured to change the temperature of the filter 332. The sensor arrangement 300A may further include a controller circuit 336 configured to control the temperature module 334 for changing the temperature of the filter 332 until the output wavelength increases with decreasing temperature. The controller circuit 336 may alternatively be configured to control the temperature module 334 for changing the temperature of the filter 332 until the proportionality constant changes from the first value to a second value. The sensor arrangement 300A may further include a determination circuit 338. The determination circuit 338 may be configured to determine the minimum value of the output wavelength and may be further configured to determine a dew point of an environment surrounding the sensor arrangement 300A, based on the minimum value of the output wavelength and the dependence. The determination circuit 338 may alternatively be configured to determine the dew point of the environment surrounding the sensor arrangement 300A, based on the temperature of the filter when the proportionality constant changes from the first value to the second value.

In other words, according to various embodiments, a sensor arrangement 300A may include a filter 332, a temperature module 334, a controller circuit 336 and a determination circuit 338. The filter 332 may be configured to provide an output signal. The filter 332 may include a waveguide or a waveguide circuit, for example a waveguide including silicon. The waveguide may be a single-mode waveguide, such as nanometer-sized waveguide. The waveguide may be patterned as at least one of a microring resonator cavity, a disk resonator cavity or a photonic crystal cavity. The filter 332 may include at least one of a microring resonator or a disk resonator. The filter 332 may include at least one of a resonator, an interferometer or a photonics crystal structure. The filter 332 may include at least one of a Mach-Zehnder interferometer or a Michelson interferometer. The output signal may be an electromagnetic wave. The output signal may be an electromagnetic wave having a wavelength in the visible range, i.e. the output signal may be an optical signal. Accordingly, the filter 332 may be an optical filter. The output wavelength may be dependent on a temperature of the filter 332. In other words, the output wavelength of the output signal may vary according to the temperature of the filter 332. The relationship between the output wavelength and the filter temperature may include a proportionality constant which may change from a first value to a second value as the filter temperature changes. The output wavelength may be directly proportional to the filter temperature. The output wavelength may decrease with decreasing temperature when the temperature of the filter is above the dew point. The output wavelength may increase with decreasing temperature when the temperature of the filter is below the dew point.

The temperature module 334 may be configured to change the temperature of the filter 332, i.e. at least one of increase or decrease the filter temperature. The temperature module 334 may be at least one of a cooler or a heater. The temperature module 334 may be configured to change the temperature of the filter 332 monotonically. The temperature module may include a cooler unit, such as a Peltier cooler. The controller circuit 336 may be configured to control the temperature module 334 for changing the temperature of the filter 332, until the output wavelength increases with decreasing temperature. The controller circuit 336 may alternatively be configured to control the temperature module for changing the temperature of the filter 332 until the proportionality constant changes from the first value to a second value. The controller circuit 336 may be software loaded onto a memory module of a computing device, or may be a hardware processor such as a microchip. The controller circuit 336 may provide control commands to the temperature module 334 so as to instruct the temperature module 334 to change the temperature of the filter 332. The controller circuit 336 may also be integral to the temperature module 334.

The determination circuit 338 may be configured to determine a minimum value of the output wavelength, and further configured to determine the dew point of the environment surrounding the sensor arrangement 300A, based on the minimum value of the output wavelength. The determination of the dew point may be further based on the dependence between the output wavelength and the temperature of the filter 332. The determination circuit 338 may be configured to determine the dew point, further based on an initial temperature of the environment. The determination circuit 338 may alternatively be configured to determine the temperature of the filter 332 when the proportionality constant changes from the first value to the second value, and use the determined temperature to determine a dew point of an environment surrounding the sensor arrangement. The dependence between the output wavelength and the temperature of the filter 332 may be a directly proportional dependence. The dependence may further be a linear dependence. The dependence may be linear before the temperature of the filter 332 reaches the dew point, i.e. when the filter 332 is warmer than the dew point. The output wavelength may decrease with decreasing temperature when the temperature of the filter 332 is above the dew point. In other words, when the filter 332 is warmer than the dew point, the output wavelength may be positively proportional to the temperature of the filter 332. When the temperature of the filter 332 is below the dew point, the output wavelength may increase with decreasing temperature. In other words, when the filter 332 is cooler than the dew point, the output wavelength may be negatively proportional to the temperature of the filter 332.

Figure 3B:
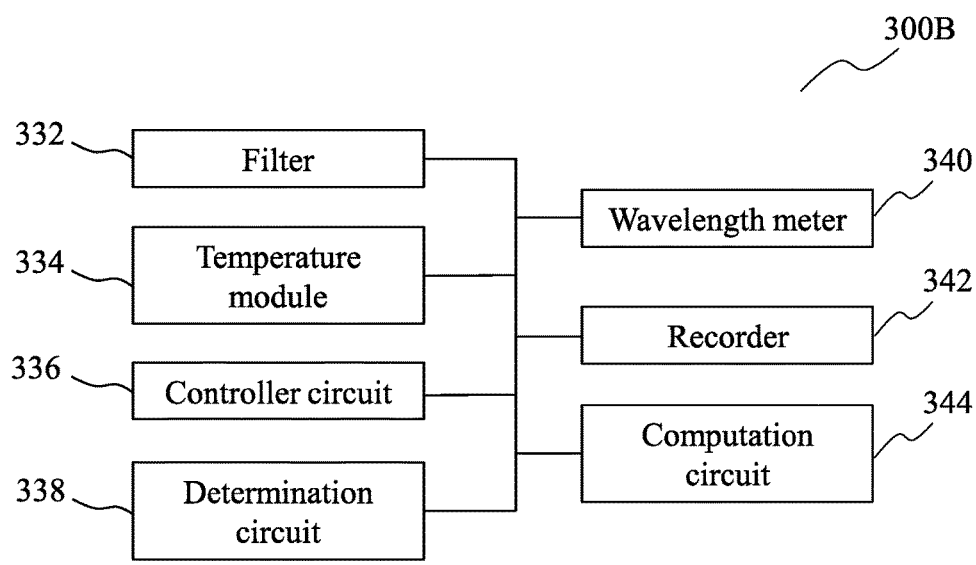
FIG. 3B shows a sensor arrangement according to various embodiments.

FIG. 3B shows a sensor arrangement 300B according to various embodiments. The sensor arrangement 300B may be similar to the sensor arrangement 300A in that it may include a filter 332, a temperature module 334, a controller circuit 336 and a determination circuit 338. As compared to the sensor arrangement 300A, the sensor arrangement 300B may further include a wavelength meter 340 configured to measure the output wavelength. The sensor arrangement 300B may further include a recorder 342 configured to record the output wavelength. The sensor arrangement 300B may further include a computation circuit 344 configured to compute a relative humidity of the environment based on the dew point.

According to various embodiments, the filter 332 of the sensor arrangement 300A or 300B may be configured to provide an output signal having an output wavelength, the output wavelength having a dependence on a temperature of the filter 332, wherein the dependence comprises a proportionality constant having a first value. The controller circuit 336 of the sensor arrangement 300A or 300B may be configured to control the temperature module 334 for changing the temperature of the filter 332 until the proportionality constant changes from the first value to a second value. The determination circuit 338 of the sensor arrangement 300A or 300B may be configured to determine a dew point of an environment surrounding the sensor arrangement, based on the temperature of the filter 332 when the proportionality constant changes from the first value to the second value.

Figure 4:
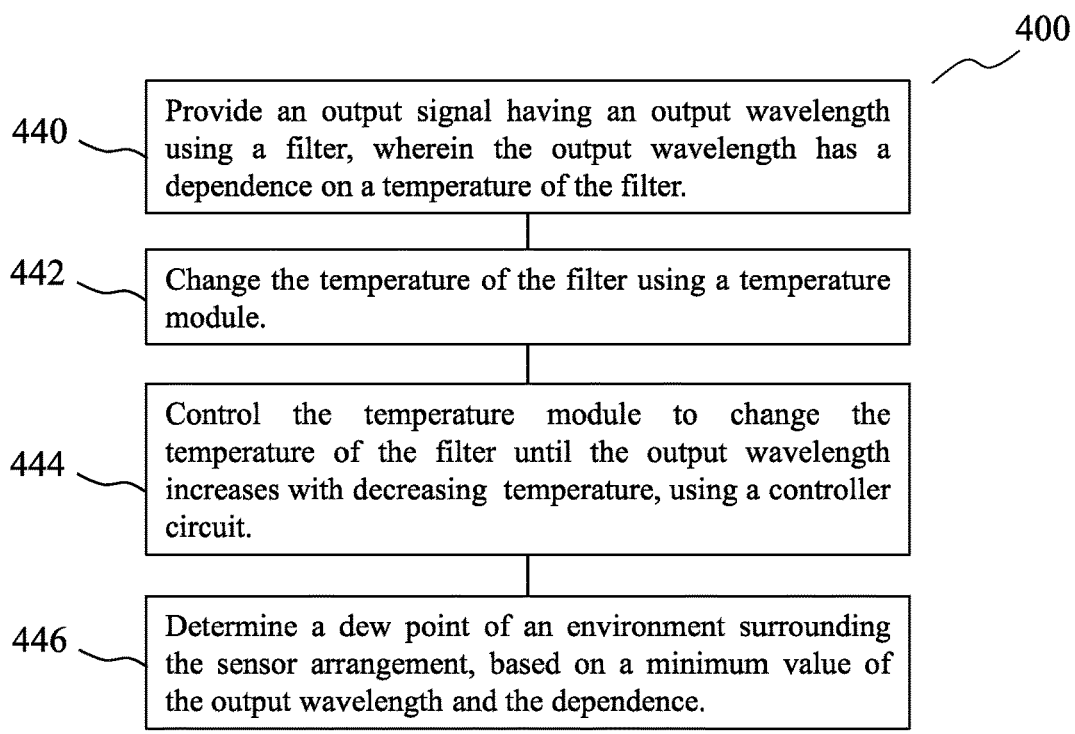
FIG. 4 shows a flow diagram showing a method of operating a sensor arrangement according to various embodiments.

FIG. 4 shows a flow diagram 400 showing a method of operating a sensor arrangement according to various embodiments. In 440, an output signal having an output wavelength may be provided using a filter. The output wavelength may have a dependence on a temperature of the filter. In 442, the temperature of the filter may be changed using a temperature module. In 444, the temperature module may be controlled to change the temperature of the filter until the output wavelength increases with decreasing temperature. The temperature module may be controlled using a controller circuit. In 446, a dew point of an environment surrounding the sensor arrangement may be determined, based on a minimum value of the output wavelength and the dependence.

Figure 5:
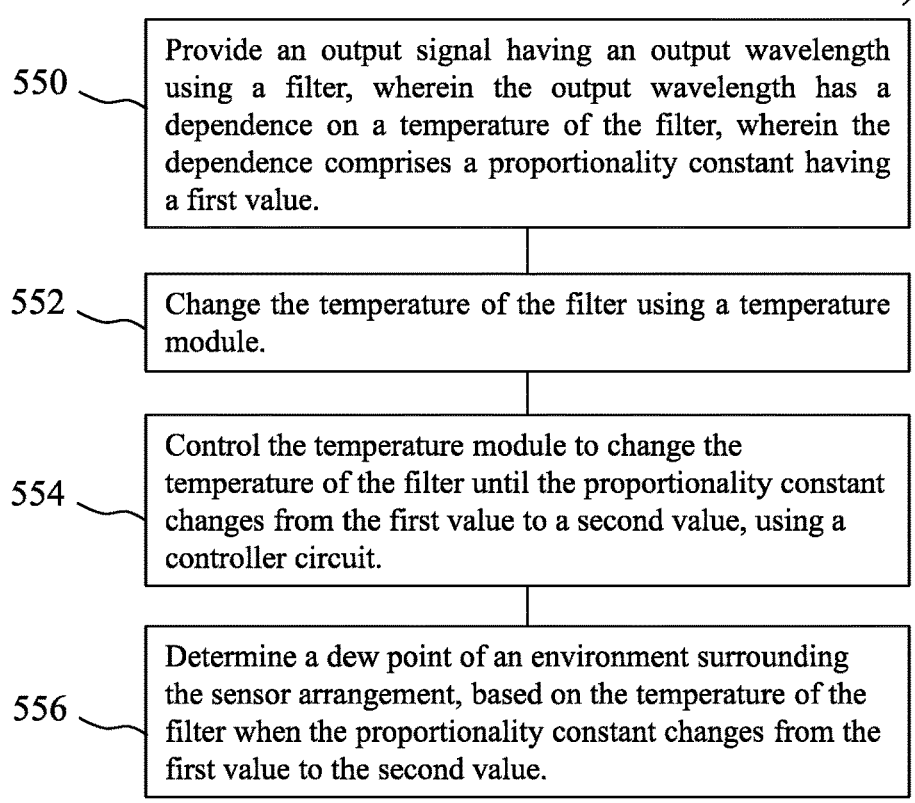
FIG. 5 shows a flow diagram showing a method of operating a sensor arrangement according to various embodiments.

FIG. 5 shows a flow diagram 500 showing a method of operating a sensor arrangement according to various embodiments. In 550, an output signal having an output wavelength may be provided using a filter. The output wavelength may have a dependence of a temperature of the filter, wherein the dependence comprises a proportionality constant having a first value. In 552, the temperature of the filter may be changed using a temperature module. In 554, the temperature module may be controlled to change the temperature of the filter until the proportionality constant changes from the first value to a second value, using a controller circuit. In 556, a dew point of an environment surrounding the sensor arrangement may be determined, based on the temperature of the filter when the proportionality constant changes from the first value to the second value.

According to various embodiments, a sensor arrangement may be provided as a miniaturized, cost-effective solution for high accuracy dew-point detection and relative humidity detection. The sensor arrangement may be the sensor arrangement 300A or the sensor arrangement 300B. The sensor arrangement may be fabricated with integrated silicon photonics technology so that the sensor arrangement may be small in dimensions while still capable of achieving high measurement accuracy. The sensor arrangement may include a partially exposed silicon microring resonator which may sense the water condensation and may also act as a self-calibrated high accuracy temperature sensor simultaneously. The dew-point value may be measured by recording resonance wavelength changes of the microring resonator. The sensor arrangement may achieve a faster response rate and a smaller physical dimension as compared with the traditional "chilled-mirror" based solutions such as the hygrometer 200A of FIG. 2A. Meanwhile, the sensor arrangement may also achieve a higher accuracy as compared to the accuracy of the miniaturized thin-film absorption based electrical relative humidity sensors, such as the humidity sensor 100 of FIG. 1.

According to various embodiments, any one of the sensor arrangements 300A or 300B may be an integrated chip sensor. The integrated chip sensor may include a nano-photonics sensing element implemented on a single chip. The nano-photonics sensing element may include the filter 332, which may be implemented on a photonics chip. The filter 332 may be a microelectromechanical systems (MEMS) device. The filter 332 may be a nano-waveguide structure. The integrated chip sensor may determine RH through wavelength detection rather than temperature sensing. The integrated chip sensor may be able to detect dew point using optical wavelength signal, independently of the cooling current. The integrated chip sensor may be able to achieve self-calibration, as the wavelength value is directly linked to the temperature value when the nano-waveguide structure is fabricated. In other words, the dependence of the output wavelength on the temperature of the filter 332 may be determined when the filter 332 is fabricated. The integrated chip sensor may be easily mass produced in a Complementary Metal-Oxide Semiconductor (CMOS) line, and may be compact in chip size. All elements of the integrated chip sensor, including light source, photonics sensing chip and wavelength detection part may be integrated on a single silicon chip. The photonics sensing chip may include the filter 332. The wavelength detection part may include the determination circuit 338 and may further include the controller circuit 336.

The design and principle of a sensor arrangement according to various embodiments will be explained in the following paragraphs.

Dew-point is the temperature at which dew forms. In other words, it is defined as the temperature at which vapor begins to condense out of the gaseous phase. It is also the temperature to which air must be cooled at constant pressure and water content to reach saturation. Dew-point is dependent on the ratio of the vapor pressure in the atmosphere to the saturation vapor pressure at the same temperature. Therefore, dew point may be used as a measure of atmospheric moisture. The concentration of moisture, hydrocarbon gases and other gases may be determined by monitoring the dew point of the gas.

Relative humidity (RH), usually expressed as a percentage, is the ratio of the water vapor pressure in the atmosphere to the saturation vapor pressure at the same temperature, which is defined as $$RH = \frac{P_w}{P_s} \times 100\% \quad (1)$$

where $P_w$ denotes the saturation vapour pressure at dew point temperature while $P_s$ denotes the saturation vapour pressure at actual air temperature. Each of $P_w$ and $P_s$ may be measured in units of hectopascals (hPa). RH is dependent on the air temperature. The air temperature may be denoted herein as $T_0$.

The saturation pressure, $P_s$ may be expressed using the Magnus formula as $$P_s = \alpha \cdot e^{\left(\frac{\beta T_0}{\lambda + T_0}\right)} \quad (2)$$

where $\alpha$, $\beta$ and $\lambda$ are the Magnus parameters.

In the temperature range of $-45°$ C. to about $+60°$ C., the Magnus parameters may be given by $\alpha=6.112$ hPa, $\beta=17.62$, and $\lambda=243.12°$ C. By restating Equation (2), the dew-point temperature, denoted herein as $T_{DP}$ and measured in units of degrees Celsius ($°$ C.), may be expressed as $$T_{DP} = \frac{\lambda \cdot \ln\left(\frac{P_w}{\alpha}\right)}{\beta - \ln\left(\frac{P_w}{\alpha}\right)} \quad (3)$$

Combining Equations (1) to (3), $T_{DP}$ may be expressed by RH and $T_0$ as $$T_{DP} = \frac{\lambda \cdot \left[\ln\left(\frac{RH}{100}\right) + \frac{\beta T_0}{\lambda + T_0}\right]}{\beta - \left[\ln\left(\frac{RH}{100}\right) + \frac{\beta T_0}{\lambda + T_0}\right]} \quad (4)$$

Figure 6:
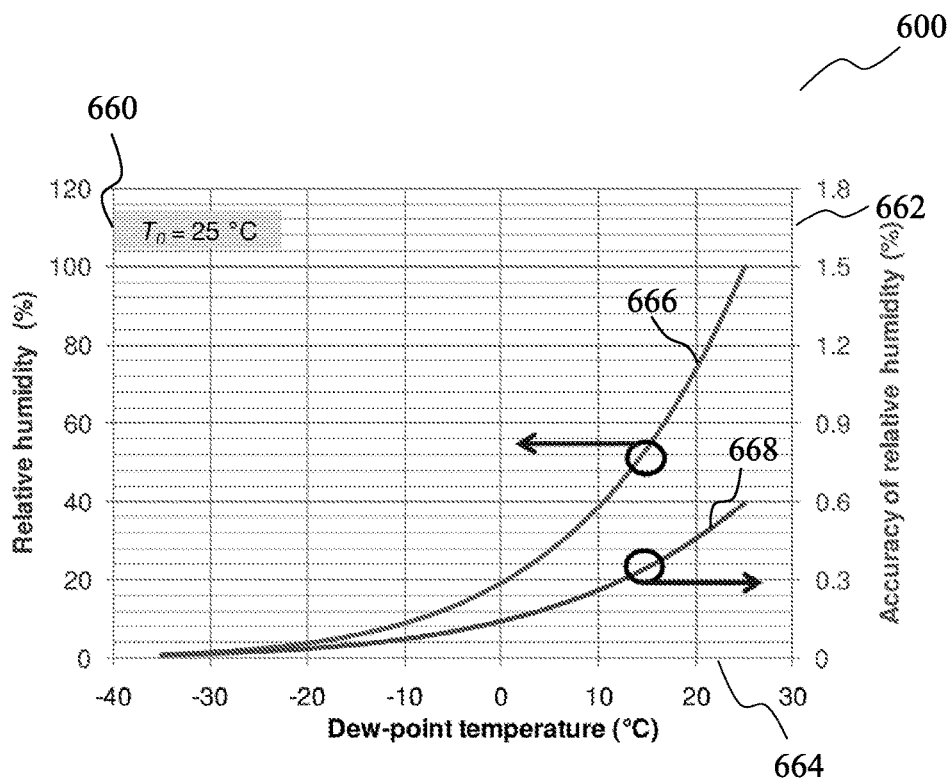
FIG. 6 shows a graph showing the relationship between dew point temperature and relative humidity, as well as the relationship between dew point temperature and the accuracy of relative humidity, when the atmospheric temperature is 25° C.

FIG. 6 shows a graph 600 showing the relationship between $T_{DP}$ and RH, as well as the relationship between $T_{DP}$ and the accuracy of RH, when $T_0$ is 25° C. The graph 600 includes a first vertical axis 660 indicating RH in %; a second vertical axis 662 indicating the accuracy of RH in %; and a horizontal axis 664 indicating $T_{DP}$ in ° C. The graph also includes a first plot 666, and a second plot 668. The first plot 666, which should be read together with the first vertical axis 660, shows the relationship between $T_{DP}$ and RH. The second plot 668, which should be read together with the second vertical axis 662, shows the absolute accuracy of RH when the $T_{DP}$ accuracy is ±0.1° C. As RH is decreased from 100% to 1%, the corresponding dew-point temperature is dropped from 25° C. to −35° C. while the detection accuracy improves from ±0.6% to ±0.014%. The second plot 668 shows that the dew-point RH sensor has a higher accuracy in a dry environment.

In silicon photonics, it is known that the refractive index of a silicon waveguide may vary as the temperature of the silicon waveguide changes. This phenomenon is known as the thermo-optic effect (TOE). In other words, the TOE refers to the thermal modulation of the refractive index of a material. A typical thermo-optic coefficient, herein denoted as of a crystal silicon based optical waveguide may be expressed as $$\frac{dn}{dT} \cong 1.8 \times 10^4 + 3.47 \times 10^{-7} - 1.98 \times 10^{-10} T^2 \quad (5)$$

In the case of a microring resonator based on a silicon waveguide, the resonance wavelength of the microring resonator may be directly linked to its temperature. The resonance wavelength may be expressed as $$\Delta \lambda = \frac{\lambda_0}{n_g} \frac{dn}{dT} \Delta T \quad (6)$$

where $\lambda_0$ denotes the resonance wavelength at initial state, $n_g$ denotes the group velocity of the light in the microring resonator, $\frac{dn}{dT}$ denotes the TOE coefficient, and $\Delta T$ denotes the temperature change. Temperature controlled photonic chips, such as optical switch, modulators and tunable optical filters, may be implemented based on the thermo-optics effect principle. Silicon photonics chips may also be used as a linear temperature sensor with very high sensitivity.

When light propagates in a waveguide, a strong evanescent wave may be generated outside the waveguide, and the characteristics of the light, including intensity, phase, and frequency, may be modulated by changing the surrounding medium. To improve the sensitivity and reduce the length of the sensing waveguide, the waveguide circuit may be patterned as at least one of a microring resonator cavity, photonic crystal cavity, or disk resonator cavity. The waveguide circuit may transfer phase changes into wavelength shift. A resonator with a high quality factor may be able to resolve the changes of the dielectric properties of the surrounding medium with very high precision via detecting the resonance wavelength shift or frequency shift.

Figure 7:
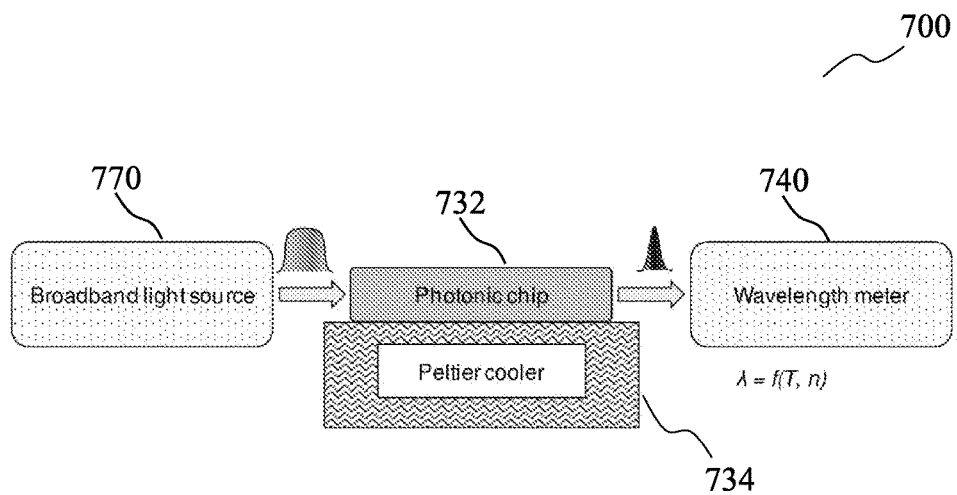
FIG. 7 shows a schematic diagram of a sensor arrangement according to various embodiments.
Figure 9:
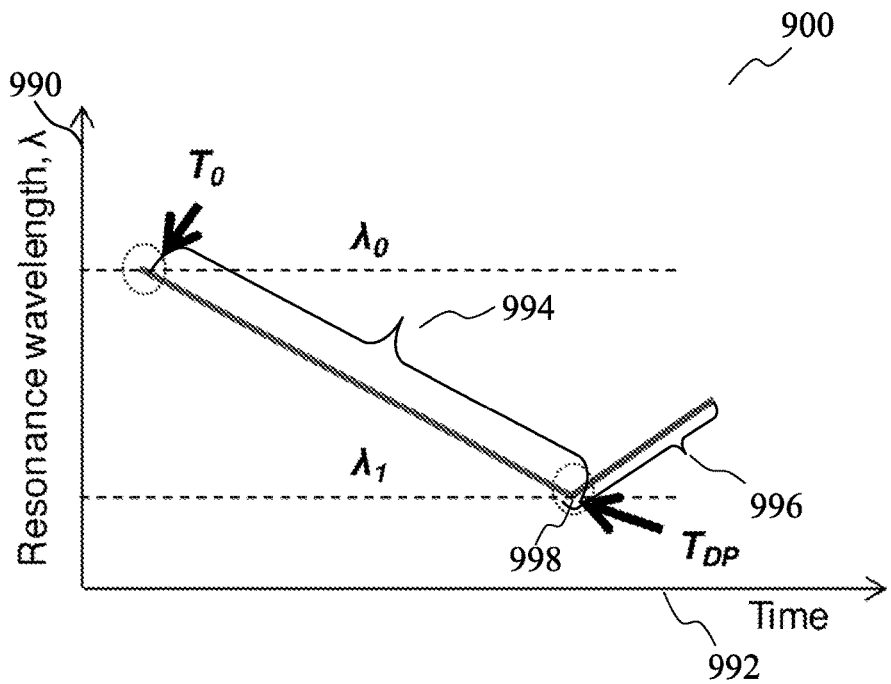
FIG. 9 shows a graph showing typical changes in the resonance wavelength over time, as recorded for a sensor arrangement according to various embodiments.

FIG. 7 shows a schematic diagram of a sensor arrangement 700 according to various embodiments. The sensor arrangement 700 may be the sensor arrangement 300A of FIG. 3A or the sensor arrangement 300B of FIG. 3B. The sensor arrangement 700 may be a high accuracy dew-point humidity detection device. The sensor arrangement 700 may include a broadband light source 770, a photonic chip 772, a wavelength meter 740 and a temperature module 734. The photonic chip 732 may include a filter that is at least substantially similar to, or identical to the filter 332 of the sensor arrangement 300A or 300B. The photonic chip 732 may include a resonator. The resonator may be the filter. The resonator may be at least one of a ring resonator, disk resonator, Mach-Zehnder interferometer, Michelson interferometer or photonics crystal structures. The resonator may also include any other photonic structures. The resonator may be a partially exposed microring resonator. The photonic chip 732 may be configured to be the sensing element of the sensor arrangement. In particular, the photonic chip 732 may be configured to sense a change in the humidity in the atmosphere, through a shift in the resonance wavelength of its resonator. The wavelength meter 740 may be at least substantially similar to, or identical to the wavelength meter 340 of the sensor arrangement 300B. The temperature module 734 may be at least substantially similar to, or identical to the temperature module 334 of the sensor arrangement 300A or 300B. The temperature module 734 may be at least one of a cooler or a heater. The temperature module 734 may be for example, a Peltier cooler. The photonic chip 732 may be arranged on the temperature module 734. The broadband light source 770 may be configured to provide a light beam and may be further configured to couple the light beam into the photonic chip 732. The photonic chip 732 may be configured to generate an output optical signal that has a periodic resonance wavelength. The resonator of the photonic chip 732 may filter an input optical signal to provide the output signal. The output optical signal with the periodic resonance wavelength may be injected into the wavelength meter 740 to record the resonance wavelength in real time. The recordings of the resonance wavelength may be plotted into a graph, for example, as shown in FIG. 9. As the photonic chip 732 is cooled-down, before its temperature reaches the dew-point, the resonance wavelength may exhibit a blue-shift as the temperature decreases, due to the TOE of silicon as explicated by Equation 6. As the photonic chip 732 is cooled down past the dew point, the resonance wavelength may exhibit a red-shift as the temperature continues to decrease, as a result of water condensation on the photonic chip 732. In other words, the output wavelength may start to increase with decreasing temperature, when the photonic chip 732 is cooled down to the dew point temperature. This wavelength shift is recorded by the wavelength meter, as shown in FIG. 9. It may also be possible that the rate of decrease of resonance wavelength with decreasing temperature greatly slows down, but does not experience a red-shift. In other words, the proportionality constant of the dependence between the output wavelength and the temperature of the photonic chip 732 may change from a first value to a second value. The second value may be lower in magnitude than the first value. This may occur when the amount of water condensation is insufficient to result in a red-shift of the resonance wavelength, for example, if the cooling power is too high and the evanescent light of the resonator is very small. Although a red-shift may not occur, the rate of decrease in the resonance wavelength may still exhibit a slow down, past the dew-point.

According to various embodiments, a broadband light emitted from a light source may be injected into the photonics chip 732, also referred herein as the photonics chip. The photonics chip may be one of a ring resonator, disk resonator, Mach-Zehnder interferometer, Michelson interferometer, photonics crystal structures or any other structures which can generate temperature (T)-dependent wavelength signals. The wavelength ($\lambda$) signal may also be significantly affected by changes in the refractive index (n) of the surroundings of the photonics chip. The wavelength signal, as modulated by the photonics chip and the refractive index changes of the surroundings of the photonics chip, may be recorded by the wavelength meter 740. Based on the relationship of $\lambda$=f(T,n), the wavelength at the initial temperature $T_0$, and the wavelength at the dew point temperature $T_{DP}$ can be expressed by $\lambda_0$ and $\lambda_1$ respectively. Therefore, the relative humidity (RH) can be expressed as RH=f($T_0,T_{DP}$)=f($\lambda_0, \lambda_1$). The dew-point may be determined more accurately, quicker and independently of cooling speed, by measuring the optical wavelengths, instead of measuring temperature.

Figure 8A:
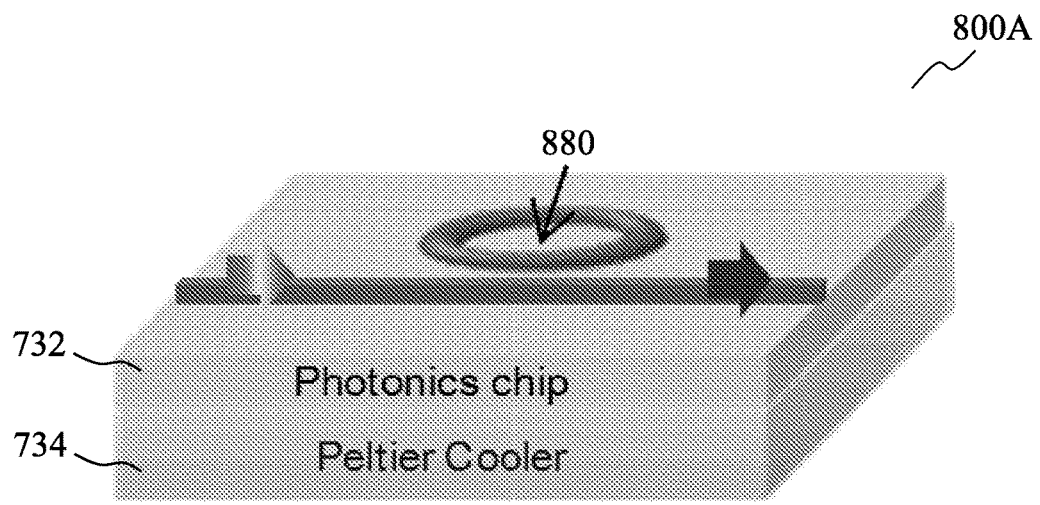
FIG. 8A shows another schematic diagram of a sensor arrangement according to various embodiments.

FIG. 8A shows another schematic diagram 800A of a sensor arrangement according to various embodiments. The sensor arrangement may be at least substantially similar to the sensor arrangement 700. The sensor arrangement may include a photonics chip 732 and a temperature module 734. The temperature module 734 may be a Peltier cooler. The photonics chip 732 may include a filter. The filter may be a resonator 880.

Figure 8B:
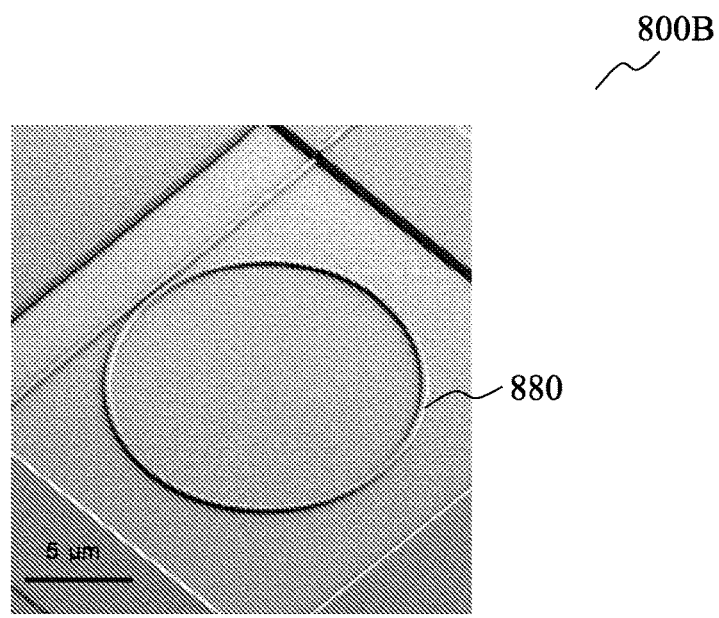
FIG. 8B shows a scanning electron microscope image of a photonics chip according to various embodiments.

FIG. 8B shows a scanning electron microscope image 800B showing a photonics chip according to various embodiments. The photonics chip may be the photonics chip 732 of FIG. 8A, which includes a resonator 880. The resonator 880 may be at least one of a microring resonator or an optical cavity such as a Fabry-Pérot cavity. The resonator 880 may resonate at a resonance frequency, such that the resonator 880 may function as a filter. The filtering function of the resonator 880 may depend on the resonance frequency of the resonator 880. In other words, the resonator 880 may receive an input light beam and generate an output light beam, wherein the output light beam has a frequency dependent on the resonance frequency. The resonance frequency of the resonator 880 may depend on a temperature of the resonator 880, and may further depend on the optical properties of matter surrounding the resonator 880. For example, the amount of condensation on the resonator 880 may affect the optical properties of the matter surrounding the resonator 880 and thereby change the resonance frequency of the resonator 880.

FIG. 9 shows a graph 900 showing typical changes in the resonance wavelength over time, as recorded for a sensor arrangement according to various embodiments. The graph 900 may be plotted from the data points recorded by the wavelength meter 740 of FIG. 7. In other words, the graph 900 shows the wavelength shift that occurred in the sensor arrangement 700 of FIG. 7. The graph 900 includes a vertical axis 990 indicating resonance wavelength; and a horizontal axis 992 indicating time. The graph 900 further includes a first plot portion 994 and a second plot portion 996. The first plot portion 994 is plotted from the time when the photonic chip 732 is at the initial temperature $T_0$, to the time when the temperature of the photonic chip 732 reaches the dew-point temperature $T_{DP}$. The second plot portion 996 is plotted from the time when the temperature of the photonic chip 732 increases from $T_{DP}$. The first plot portion 994 reflects the "blue-shift" of the output signal while the second plot portion 996 reflects the "red-shift" of the output signal.

When the photonic chip is cooled to the dew-point temperature, some water molecules may be condensed on the filter, which increases the effective index of the filter structure abruptly because of the higher refractive index of water. The filter may be the microring resonator. The refractive index of water is about 1.32 while the refractive index of air is 1. As a result, the resonance wavelength of the filter may exhibit a red-shift. In other words, the resonance wavelength of the resonator increases. The red-shift of the resonance wavelength is indicated by the second plot portion 996. The dew-point temperature information may be derived by recording the inflection point 998 accordingly. Through the relationship between dew-point and relative humidity given by Equation (4), the RH value may be obtained. As the measurements relate to optical wavelengths and does not involve the measurement of 'absolute' temperatures, the accuracy of the sensor arrangement 700 in determining relative humidity may be greatly improved over conventional humidity sensors.

In the following, the experimental results of a sensor arrangement according to various embodiments will be described.

Figure 10:
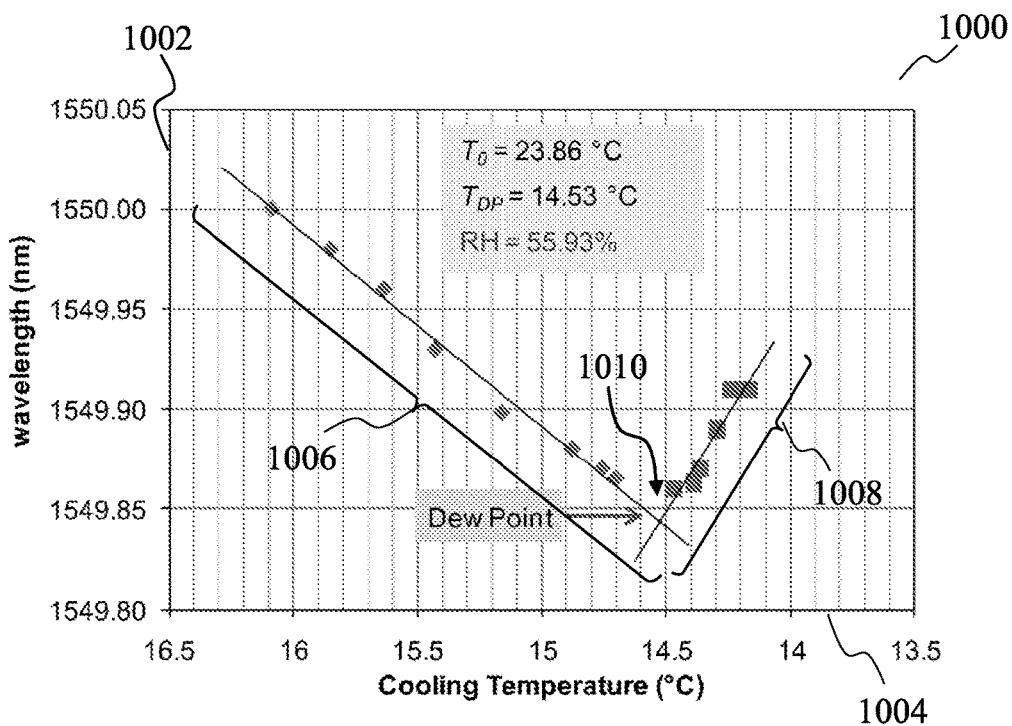
FIG. 10 shows a graph showing the dew-point determined using a prototype relative humidity sensor.

FIG. 10 shows a graph 1000 showing the dew-point measured using a prototype RH sensor. The prototype RH sensor may be at least substantially similar to the sensor arrangements 300A, 300B or 700. The graph 1000 includes a vertical axis 1002 indicating wavelength in nanometers; and a horizontal axis 1004 indicating cooling temperature in ° C. The graph 1000 further includes a first plot portion 1006, and a second plot portion 1008. An intersection between the first plot portion 1006 and the second plot portion 1008, in other words, the wavelength inflection point 1010, denotes the dew point. The wavelength inflection point 1010 was a result of water condensation accumulating on the filter, i.e. the resonator when the photonics chip was cooled down to the dew point. In the experiment, the environmental temperature, in other words, the initial temperature, $T_0$, was 23.86° C. The temperature at wavelength inflection point 1010 was 14.53° C. The RH derived from these parameters using Equation (4) is about 55.93%.

A chilled-mirror" dew-point sensor, such as the chilled-mirror" dew-point hygrometer 200A, may face inaccuracies in its measurements due to errors associated with thermal management, especially when the dew-point is very low. There may be a small difference in temperature between the "chilled-mirror" and the embedded thermistor, due to thermal distribution issues. The same issue may also occur if a thermistor is placed under the filter to detect the dew-point, due to uneven thermal distribution and slow conducting of heat between the filter and the thermistor. The sensor arrangement according to various embodiments may overcome the abovementioned problem by employing the TOE to present the real temperature of the filter, where a relationship between the resonance wavelength and the temperature of the filter is defined. The filter may be a resonator, and may include a waveguide. The resonator may be a microring resonator. The sensor arrangement may not encounter thermal distribution-associated errors, as the sensor arrangement determines the temperature of the filter using the filter itself. It may be regarded as a self-calibration process for high accuracy dew-point detection.

Figure 11:
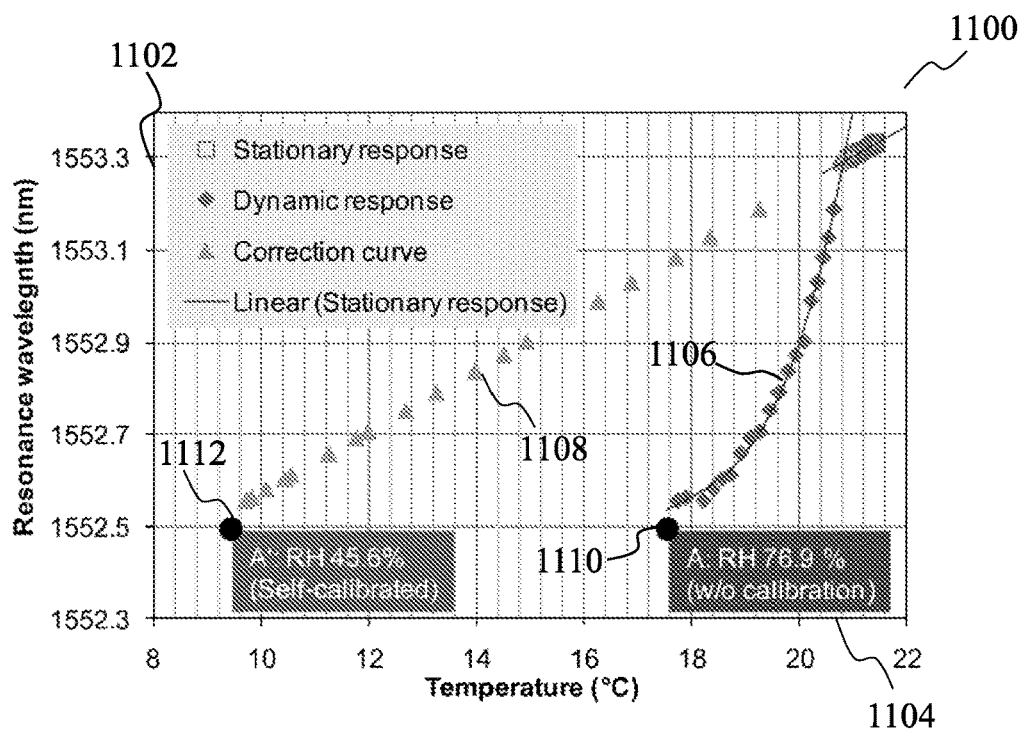
FIG. 11 shows a graph showing the results of self-calibration of a filter according to various embodiments.

FIG. 11 shows a graph 1100 showing the results of self-calibration of a filter according to various embodiments. The filter may be a microring resonator. The filter may act as a linear temperature sensor based on the principle of TOE. The graph 1100 includes a vertical axis 1102 indicating resonance wavelength of the resonator; and a horizontal axis 1104 indicating temperature in ° C. The graph 1100 includes a first plot 1106 composed of rhombuses, and a second plot 1108 composed of triangles. The first plot 1106 depicts the dynamic response of resonance wavelength against temperature, as measured by a thermistor. The second plot 1108 shows the corrected response of resonance wavelength against temperature as obtained based on the resonance wavelength and the relationship between the resonance wavelength and the temperature of the filter Comparing the first plot 1106 and the second plot 1108, it can be seen that the first plot shows an error with the measured RH value of 76.9% at point A 1110. After including the TOE calibration, the real RH value of 45.6% at point A' 1112 is obtained.

FIGS. 12 to 15 show dew-point measurement according to the sensor spectrum response at different temperatures, for sensor arrangements according to various embodiments.

Figure 12:
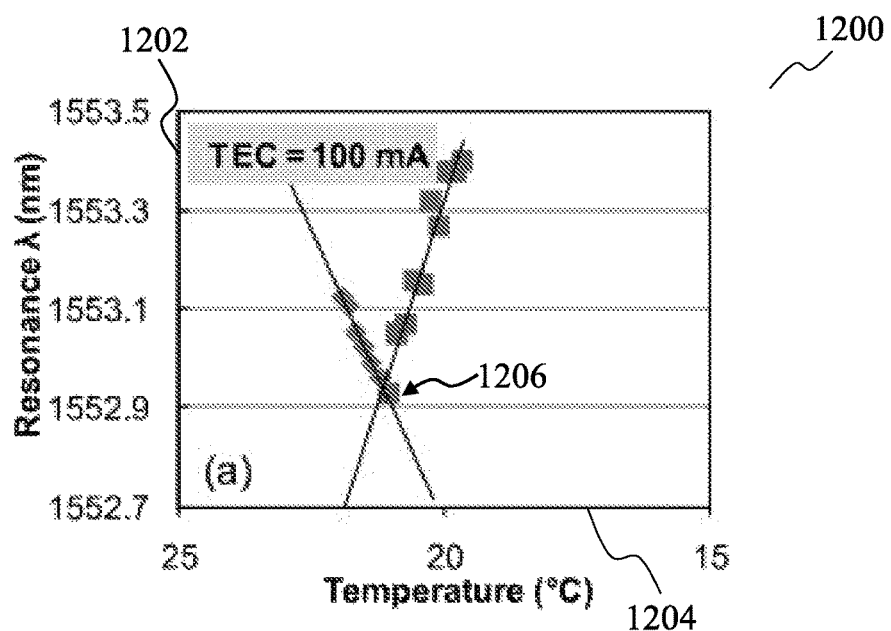
FIG. 12 shows a graph showing the changes in the resonance wavelength as the temperature of the filter decreases, when the thermoelectric cooling (TEC) current is 100 mA.

FIG. 12 shows a graph 1200 showing the changes in the resonance wavelength as the temperature of the filter decreases, when the thermoelectric cooling (TEC) current is 100 mA. The graph 1200 includes a vertical axis 1202 indicating resonance wavelength in nm; and a horizontal axis 1204 indicating temperature in ° C. The inflection point 1206 corresponds to a resonance wavelength of about 1552.9 nm.

Figure 13:
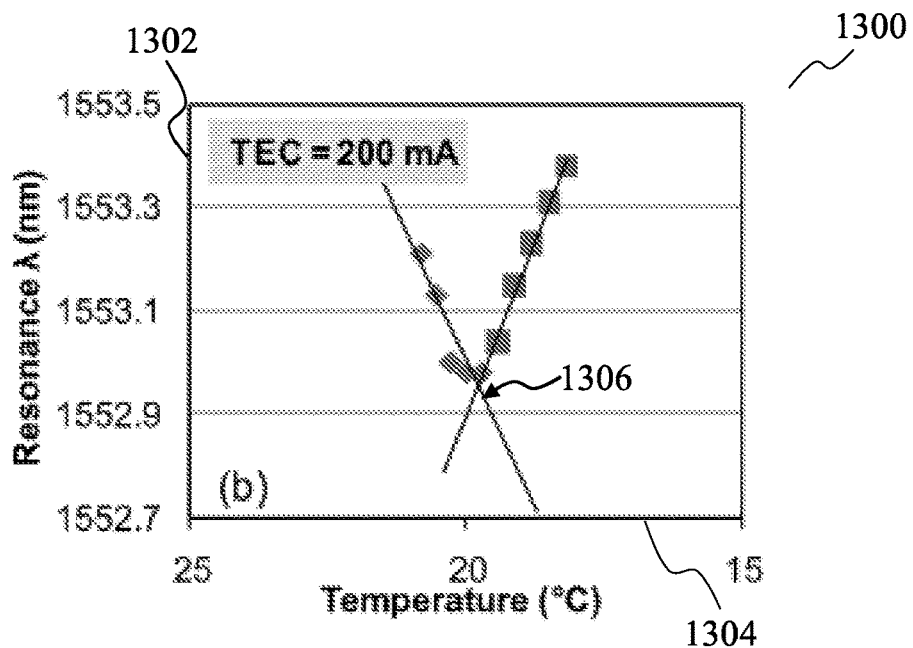
FIG. 13 shows a graph showing the changes in the resonance wavelength as the temperature of the filter decreases, when the TEC current is 200 mA.

FIG. 13 shows a graph 1300 showing the changes in the resonance wavelength as the temperature of the filter decreases, when the TEC current is 200 mA. The graph 1300 includes a vertical axis 1302 indicating resonance wavelength in nm; and a horizontal axis 1304 indicating temperature in ° C. The inflection point 1306 corresponds to a resonance wavelength of slightly above 1552.9 nm.

Figure 14:
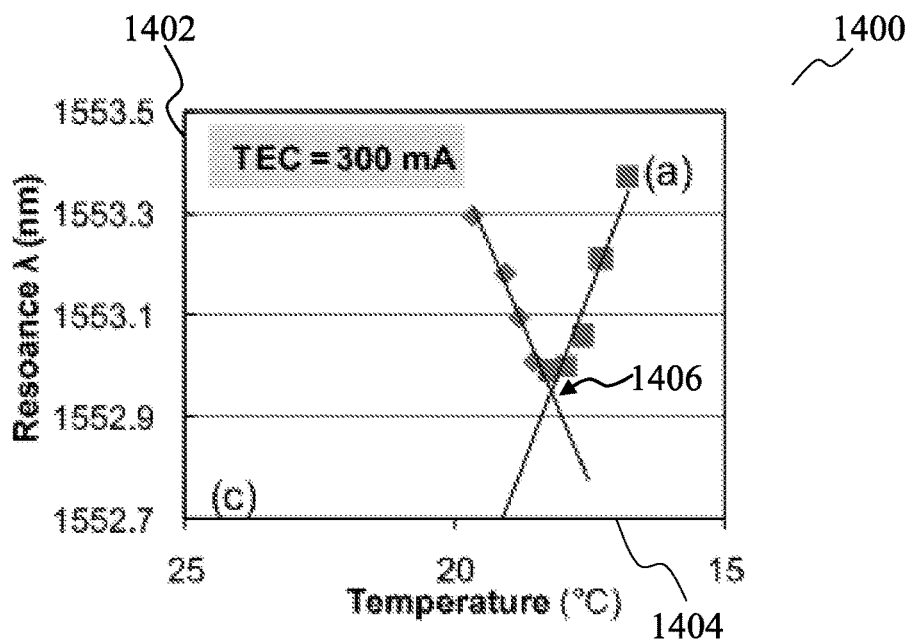
FIG. 14 shows a graph showing the changes in the resonance wavelength as the temperature of the filter decreases, when the TEC current is 300 mA.

FIG. 14 shows a graph 1400 showing the changes in the resonance wavelength as the temperature of the filter decreases, when the TEC current is 300 mA. The graph 1400 includes a vertical axis 1402 indicating resonance wavelength in nm; and a horizontal axis 1404 indicating temperature in ° C. The inflection point 1406 corresponds to a resonance wavelength of slightly above 1552.9 nm.

Figures 15, 16:
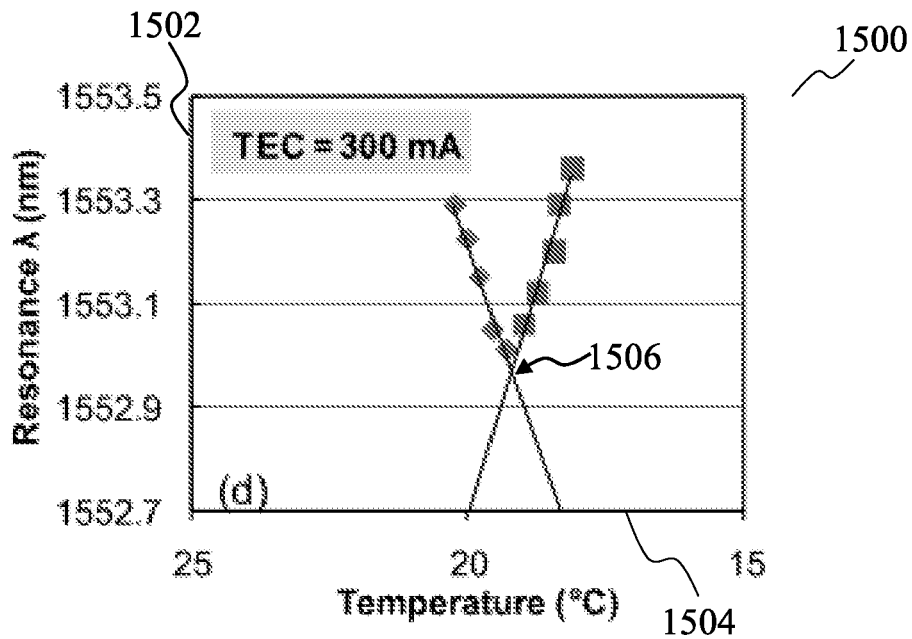
FIG. 15 shows a graph showing the changes in the resonance wavelength as the temperature of the filter decreases, when the TEC current is 300 mA.
FIG. 16 shows a table showing the typical standard deviation in the measurements of a sensor arrangement according to various embodiments.

FIG. 15 shows a graph 1500 showing the changes in the resonance wavelength as the temperature of the filter decreases, when the TEC current is 300 mA. The graph 1500 includes a vertical axis 1502 indicating resonance wavelength in nm; and a horizontal axis 1504 indicating temperature in ° C. The data points of the graph 1500 were recorded under the same cooling conditions as the data points of graph 1400. The inflection point 1506 corresponds to a resonance wavelength of slightly above 1552.9 nm, similar to the inflection point 1406 of the graph 1400. As can be seen, the sensor arrangement is able to achieve consistent repeatability of the inflection point. Although the temperatures given by the thermistor in the graph 1500 are different from the temperatures given by the thermistor in the graph 1400, the inflection point of the resonant wavelength as indicated by the horizontal axis in the graph 1500 is at least substantially similar to the inflection point of the resonant wavelength as indicated by the horizontal axis in the graph 1400.

As can be seen from FIGS. 12 to 15, the changes in the output wavelength generally follow the same pattern, irrespective of the rate of temperature change in the environment as controlled by the TEC current. In all of these graphs 1200 to 1500, the output wavelength always experiences a blue-shift, followed by a red-shift as the environmental temperature cools down. And more importantly, the inflection point (i.e. from blue-shift to red shift) is almost corresponding to a constant wavelength, indicating the dew-point. Nevertheless, it may be possible that the red-shift does not occur, such as when the amount of condensation on the filter is too small, when the cooling power is too high or when the evanescent light of the resonator is very small. In such cases, the dew point can still be determined by identifying the point where the rate of change in the output wavelength changes. For example, the output wavelength in the usual blue-shift region may have a first rate of change, i.e. proportionality constant of a first value, and when the temperature of the filter drops below the dew point temperature, the output wavelength exhibits a different rate of change in relation to temperature, i.e. proportionality constant of a second value. The rate of change in the output wavelength may slow down substantially at below the dew point temperature.

FIG. 16 shows a table 1600 showing the typical standard deviation in the measurements of a sensor arrangement according to various embodiments. As can be seen in the table 1600, the standard deviation in the resonance wavelength measurement is about 0.0125 nm while the standard deviation in the dew-point temperature is about 0.19° C. Accordingly, the standard deviation of the derived RH is about ±0.13%, which is much lower than the typical value of ±5% of state of the art humidity sensors. The sensor arrangement may achieve a higher accuracy than state of the art humidity sensors, in the determination of RH.

According to various embodiments, the sensor arrangement may achieve advantages over existing RH sensors, in terms of sensor size, cost, and accuracy. The sensor arrangement may meet the requirements of many applications for high-end users. The sensor arrangement may achieve an accuracy level of ±0.2° C. at 45% RH. The sensor arrangement may also have a quick response time of about 2 to 5 seconds. The sensor arrangement may be small in size, for example 3 mm×1.9 mm×0.9 mm. The sensor arrangement may be achievable at a cost of about US$10-30.

According to various embodiments, the sensor arrangement may be achieved through a chip-level solution. Using the TOE and wavelength detection method, the sensor arrangement may achieve a high accuracy detection of RH, powered by self-calibration. The sensor arrangement may be a disruptive solution for sustaining growth for accurate and reliable moisture measurement in aerospace, meteorology, natural gas, automotive, petrochemical, agriculture, biology, pharmaceutical and environmental sensing, such as indoor air quality monitoring.

While embodiments of the invention have been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced. It will be appreciated that common numerals, used in the relevant drawings, refer to components that serve a similar or the same purpose.

What is claimed is:

1. A sensor arrangement comprising:
   a filter configured to modulate an electromagnetic wave at least partially based on a temperature of the filter;
   a temperature control module configured to change the temperature of the filter;
   a controller circuit configured to control the temperature control module to change the temperature of the filter until a wavelength of the modulated electromagnetic wave increases with decreasing temperature after reaching a minimum value; and
   a determination circuit configured to determine a dew point of an environment surrounding the sensor arrangement, based on the minimum value of the wavelength.

2. The sensor arrangement of claim 1, wherein the wavelength decreases with decreasing temperature when the temperature of the filter is above the dew point.

3. The sensor arrangement of claim 1, wherein the wavelength increases with decreasing temperature when the temperature of the filter is below the dew point.

4. The sensor arrangement of claim 1, further comprising a wavelength meter configured to measure the wavelength.

5. The sensor arrangement of claim 1, further comprising a recorder configured to record the wavelength.

6. The sensor arrangement of claim 1, further comprising a computation circuit configured to compute, a relative humidity of the environment based on the dew point.

7. The sensor arrangement of claim 1, wherein the determination circuit is further configured to determine the minimum value of the wavelength.

8. The sensor arrangement of claim 1, wherein the wavelength of the modulated electromagnetic wave has a first linear dependence on the temperature of the filter when the temperature of the fitter is below the dew point and wherein the wavelength of the modulated electromagnetic wave has a second linear dependence on the temperature of the filter when the temperature of the filter is above the dew point.

9. The sensor arrangement of claim 1, wherein the determination circuit is configured to determine the dew point, further based on an initial temperature of the environment.

10. The sensor arrangement of claim 1, wherein the filter is an optical filter.

11. The sensor arrangement of claim 1, wherein the filter is a microelectromechanical systems device.

12. The sensor arrangement of claim 1, wherein the filter comprises a waveguide.

13. The sensor arrangement of claim 1, wherein the filter comprises at least one of a resonator, an interferometer or a photonics crystal structure.

14. The sensor arrangement claim 1, wherein the filter comprises at east on of a microring resonator or a disk resonator.

15. The sensor arrangement of claim 1, wherein the filter comprises at least one of a Mach-Zehnder interferometer or a Michelson interferometer.

16. The sensor arrangement of claim 1, wherein the temperature control module changes the temperature of the filter monotonically.

17. The sensor arrangement of claim 1, wherein the temperature control module comprises a cooler unit.

18. The sensor arrangement of claim 1, wherein the filter comprises a waveguide configured to modulate the electromagnetic wave, wherein a refractive index of the waveguide is dependent on the temperature of the filter.

19. A method of operating a sensor arrangement, the method comprising:
   modulating an electromagnetic wave at least partially based on a temperature of a filter;
   changing the temperature of the filter using a temperature module;
   controlling the temperature module to change the temperature of the filter until the wavelength increases with decreasing temperature after reaching a minimum value using a controller circuit; and
   determining a dew point of an environment surrounding the sensor arrangement, based on the minimum value of the wavelength.

20. A sensor arrangement comprising:
   a filter configured to modulate an electromagnetic wave at least partially based on a temperature of a filter,
   wherein a wavelength of the modulated electromagnetic wave depends on the temperature of the filter, the dependence comprising a proportionality constant;
   a temperature control module configured to change the temperature of the filter;
   a controller circuit configured to control the temperature control module to change the temperature of the filter until the proportionality constant changes from a first value to a second value; and
   a determination circuit configured to determine a dew point of an environment surrounding the sensor arrangement, based on the temperature of the filter when the proportionality constant changes from the first value to the second value.

* * * * *